(12) United States Patent
Serdyuk

(10) Patent No.: US 6,833,377 B2
(45) Date of Patent: Dec. 21, 2004

(54) COMPOSITION AND METHOD FOR POTENTIATING DRUGS

(75) Inventor: Sergey Serdyuk, Jerusalem (IL)

(73) Assignee: Gevys Pharmaceuticals Ltd., Jerusalem (IL)

( * ) Notice: Subject to any disclaimer, the term of this patent is extended or adjusted under 35 U.S.C. 154(b) by 223 days.

(21) Appl. No.: 09/775,794

(22) Filed: Feb. 5, 2001

(65) Prior Publication Data

US 2003/0004134 A1 Jan. 2, 2003

(51) Int. Cl.[7] .............................................. A61K 31/445
(52) U.S. Cl. .......................... 514/327; 514/59; 514/626
(58) Field of Search ............................ 514/59, 327, 626

(56) References Cited

U.S. PATENT DOCUMENTS

| | | | |
|---|---|---|---|
| 3,947,579 A | 3/1976 | Fuxe | 514/327 |
| 4,788,189 A | 11/1988 | Glazer | 514/221 |
| 4,843,071 A | 6/1989 | Hohenwarter | 514/217 |
| 4,952,402 A | 8/1990 | Sparks et al. | 424/484 |

(List continued on next page.)

FOREIGN PATENT DOCUMENTS

| | | | | |
|---|---|---|---|---|
| EP | 714663 A2 | 6/1996 | ......... | A61K/45/06 |
| WO | WO 01/34603 A2 | 5/2001 | | |

OTHER PUBLICATIONS

Goyagi et al., "The Addition of Epinephrine Enhanced Postoperative Analgesia by Intrathecal Morphine", Anesth. Analg, vol. 81, pp. 508–513, 1995.
Krupina et al., "Effect of melipramine on the development of experimental depressive syndrome in rats induced by a systematic administration of 1–methyl–4–phenyl–tetrahydropyridine (MPTP)", vol. 8, pp. 159–165 (1995).
Mancusi et al., "Anestesia subarachnoidea e midodrina", Min. Anest, vol. 53, pp. 19–26, (1987).
Fredriksson et al., "Synergistic interactions between NMDA–antagonists and L–Dopa on Activity in MPTP––treated mice", J Neural Transm [GenSect], vol. 97, pp. 197–209, (1994).
Kaminski et al., "Effect on Non–Steroidal Anti–Inflammatory Drugs on the Anticonvulsive Activity of Valproate and Diphenylhydantoin Against Maximal Electroshock–Induced Seizures in Mice", Pharmacological Research, vol. 37, No. 5, pp. 375–381, (1998).
Winter et al., "The Acute Effect of Monoamine Reuptake Inhibitors of the Stimulus Effects of Hallucinogens", Pharmacology of Biochemistry and Behavior, vol. 63, No. 3, pp. 506–513, (1999).
Niemi et al., "Adrenaline markedly improves thoracic epidural analgesia produced by a low–dose infusion of bupivacaine, fentanyl and adrenaline after major surgery", Acta Anaesthesiologica Scandinavica, vol. 42, pp. 897–909, (1998).

Freedman et al. "Improving Patient–Controlled Analgesia: Adding Droperidol to Morphine Sulfate to reduce Nausea and Vomiting and Potentiate Analgesia", The Mount Sinai Journal of Medicine, vol. 62, No. 3, (1995).
Parsons et al., "Comparison of the potency, Kinetics and voltage–dependency of a Series of Uncompetitive NMDA Receptors Antagonists In Vitro with Anticonvulsive and Motor Impairment Activity In Vivo", Neuropharmacology, vol. 34, No. 10, pp. 1239–1258, (1995).
Woolf et al., "Naloxone–Reversible Peripheral Electroanalgesia in intact and Spinal Rats", European Journal of Pharmacology, vol. 45, pp. 311–314, (1977).
Campbell et al., "Dose–Catalepsy Response to Haloperidol in Rat: Effect of Strain and Sex", Neuropharmacology, vol. 27, No. 11, pp. 1197–1199, (1988).
Coderre et al., "Cutaneous hyperalgesia: contributions of the peripheral and central nervous systems to the increase in pain sensitivity after injury", Brain Research, vol. 404, pp. 95–106, (1987).
Kuczenski et al., "Amphetamine–Haloperidol Interactions in Rat Striatum: Failure to Correlate Behavioral Effects with Dopaminergic and Cholinergic Dynamics", Brain Research, vol. 126, pp. 117–129, (1977).
Porsolt et al., "Behavioural Despair in Rats: A New Model Sensitive to Antidepressant Treatment", European Journal of Pharmacology, vol. 47, pp. 379–391, (1978).
Lapin et al., "Effect of D1 and D2 dopamine receptor antagonists and catecholamine depleting agents on the locomotor stimulation induced by dizocilpine in mice", Behavioural Brain Research, vol. 70, pp. 145–151, (1995).
Serdyuk et al., "Gastric Afferents Participate in Regulation of Individual Sensitivity to Stress Exposure Due to Change of Cardiopulmonary Reflex", Behavioral Pharmacology, vol. 6, No. 1, pp. 152, (1995).
Huang et al., "Influence of epinephrine as an adjuvant to epidural morphine for postoperative analgesia", Ma Zui Xue Za Ahi, vol. 31, No. 4, pp. 245–248, (1993).
Sills et al., "Subchronic fluoxetine treatment induces a transient potentiation of amphetamine–induced hyperlocomotion: possible pharmacokinetic interaction", Behav. Pharmacol., vol. 11, No. 2, pp. 109–116, (2000).
Ossowka, K., "The role of excitatory amino acids in experimental models of Parkinson's disease," J. Neutral Transm [P–D Sect], (1994) 8:39–71.

Primary Examiner—Dwayne Jones
(74) Attorney, Agent, or Firm—Browdy and Neimark, PLLC

(57) ABSTRACT

A method of potentiating the activity of a drug which affects the central nervous system. (CNS) comprising systemically administrating to a subject said drug together with an effective amount of a compound which affects peripheral chemoreceptors and, optionally, with an effective amount of a stimulator of osmoreceptors. Also disclosed are pharmaceutical compositions for systemic administration comprising a CNS drug together with the aforementioned compounds.

12 Claims, No Drawings

U.S. PATENT DOCUMENTS

| | | | |
|---|---|---|---|
| 5,314,884 A | 5/1994 | Seidel et al. | 514/252 |
| 5,431,922 A | 7/1995 | Nicklasson | 424/490 |
| 5,552,429 A | 9/1996 | Wong et al. | 514/415 |
| 5,891,842 A | 4/1999 | Kream | 514/7 |
| 5,942,241 A | 8/1999 | Chasin et al. | 424/44 |
| 6,022,562 A | 2/2000 | Autant et al. | 424/409 |

COMPOSITION AND METHOD FOR POTENTIATING DRUGS

FIELD OF THE INVENTION

This invention relates to compositions and methods useful for potentiating the activity of drugs affecting the Central Nervous System.

BACKGROUND OF THE INVENTION

The following is a list of references which may be important in understanding the background of the invention:

1. U.S. Pat. No 5,942,241;
2. Mancusi L. et al., Minerva Anestesiol, 53(1–2) 19–26, 1987;
3. Huang KS et al., Ma Tsui Hsueh Tsa Chi, 31(4), 245–8, 1993;
4. Goyagi T et al., Anesth Analg. 81(3), 508–13, 1995;
5. Niemi G et al., Acta Anaesthesiol Scand, 42(8), 897–909, 1998;
6. Russian Patent No. SU 2,088,233
7. $8^{th}$ Sardinian Conference on Neuroscience. *Anxiety and depression neurobiology pharmacology; and clinic.* Tanka Village, Villasimius, May 24–$28^{th}$ 1995. Behavioral Pharmacology, Vol. 6 (Supplement 1), 1995, P.152.

The references are referred to in the specification by their respective numbers.

Currently, two principal methods of potentiation of the effect of central nervous system (CNS) active drugs (potentiated synergism) are known: (1) pharmacokinetic; and (2) pharmacodynamic.

The pharmacokinetic method provides potentiation by creating a maximum concentration of the drug at the site of the primary pharmacological response due to improved absorption, increased bioavailability, accelerated distribution and retarded elimination of the drug (Goodman & Gilman's *The Pharmacological Basis of Therapeutics* 9th ed. Hardman Paperback, McGraw-Hill Book Company, 1996). The known methods of pharmacokinetic potentiation are connected, as a rule, with the development of new and improved dosage forms and ways of drug administration.

In recent years, the method of controlled extended release of active ingredients from micro-particles and microcapsules (e.g. U.S. Pat. No. 6,022,562) has been considered the most popular and promising of these methods. Each microparticle generally represents a matrix of nontoxic polymer containing a drug and osmotically active polyatomic alcohols (e.g. U.S. Pat. No. 5,431,922). Micro-particles are included in traditional dosage forms for oral administration. (tablets, capsules, suspensions, granules), which most frequently contain polymers such as polyvinylpyrilidone (PVP) or polyethylene oxide (PEO), and osmotically active alcohols such as sorbitol, xylitol and mannitol.

The main drawback of this method is the necessity for permanent administration of a high dose of the active ingredient. This may lead, in the case of long-term administration, to the potentiation not only of its therapeutic action, but also of side effects in case of poor selectivity of the drug effect. In addition, the production of traditional oral dosage forms on the basis of micro-particles and microcapsules leads to a manifold increase in their cost, which often greatly exceeds the cost of the active ingredient. Despite its numerous advantages the aforementioned pharmacokinetic method does not achieve a manifold intensification of the effect of drugs.

Osmotically active polymers (PVP, PEO) and polyatomic alcohols (xylitol, sorbitol, mannitol), included in the composition of both traditional monolithic dosage forms as well as forms intended for controlled release of active ingredients, play an important role in pharmacokinetic potentiation of CNS active drugs (e.g. U.S. Pat. Nos. 4,952,402 and 5,552,429). However, they are not active components of the compositions but rather they only provide optimal conditions for the pharmacokinetics of a CNS active drug.

A combined application of the α-1-adrenomimetics phenylephrine or midodrine, as well as the nonselective adrenomimetic adrenaline together with narcotic analgesics and local anesthetics has been found to lead to a pharmacokinetic potentiation of analgesic and anesthetic effect. However, these compositions were only administered locally to intensify local anesthesia (1) or intrathecally to intensify spinal anesthesia (2–5). intensification and prolongation of the effect of analgesics and anesthetics was caused by an increase in their local concentration, which is due to a decrease in the amount of analgesics and anesthetics entering the blood as a result of a local spasm of vessels caused by the adrenomimetics.

The pharmacodynamic method also provides potentiation by a joint administration of active ingredients causing unidirectional pharmacological effects, but affecting different molecular substrates (having different mechanisms) (Goodman & Gilman's The Pharmacological Basis of Therapeutics, op. cit.)

Two main types of pharmacodynamic methods of the potentiation of CNS active drugs are known:

(1) Potentiation of the effects of CNS active drugs caused by joint administration of CNS active drugs only;

(2) Potentiation of the effects of CNS active drugs caused by joint administration of a CNS active drug and a peripherally active drug.

The well-known first method consists in joint administration of two CNS active drugs that act unidirectional and mutually potentate each other's effect. In cases of grave depressions, pain syndrome, parkinsonism, epilepsy and psychoses, potentiation of the maximal effect of antidepressants, neuroleptics, analgesics, psychostimulants, anti-parkinson and anticonvulsive agents is required. As a rule, potentiation is possible only by joint administration of CNS active drugs in submaximal doses. Potentiating of submaximal doses effects of CNS active drugs results in maximum possible intensification of their therapeutic activity On the other hand potentiating of their central toxic effect is also caused resulting in multiple side effects and complications. (e.g. U.S. Pat. No. 4788189; Winter J. C. et al., Pharmacol Biochem Behav, 63(3). 507–13, 1999; Sills T S et al., Behav Pharmacol, 11(2), 109–16, 2000); Fredriksson A. et al., J Neural Transm Cen Sect, 97(3), 197–209, 1994).

U.S. Pat. No. 3,947,579 discloses a method for potentiating the neuroleptic activity of drugs such as butyrophenone derivatives by administrating them together with an amino acid known to cross the blood brain barrier and have muscle relaxant properties useful in the treatment of spinal origin spasticity.

At mild and moderate severity (or stage) of a disease, maximal or even submaximal effect caused by CNS active drug is quite sufficient. In this case therapeutic activity may usually be achieved by potentiating threshold doses of CNS active drugs. (e.g. U.S. Pat. No. 5,891,842; Freedman G. M., Mt. Sinai J Med, 62(3), 221–5, 1995; Kaminsky R et al., Pharmacol Res, 37(5), 375–81, 1998). The potentiation of the effect of threshold doses significantly reduces the probability of the development of side effects and complications inherent to CNS active drugs at maximal doses, as well as the development of tolerance and dependence due to their prolonged administration. However, even this, the safest of all known methods of pharmacodynamic potentiation has its own drawbacks:

1) The effect achieved by potentiating low doses of drugs does not exceed, as a rule, the maximal effect of the drug itself
2) When the elimination of active ingredients is decelerated (childhood age, diseases of liver or kidneys) or the permeability of the hematoencephalic barrier is increased, threshold dosages of CNS active drugs can become submaximal and even toxic in their effect. Therefore, their combined administration even at such threshold doses becomes impossible due to the potentiation of their CNS side effects.
3) The risk of potentiating not only therapeutic, but also toxic effects of CNS active drugs by even small doses of other safe CNS active drugs.

The potentiation of the effects of threshold doses of CNS active drugs can also be realized by a combined administration of a CNS active and a peripherally osmotically active drug. It is known that oral or intramuscular administration of osmotically active copolymers of N-vinyl-pyrrolidone with N,N,N,N, triethylmethacryloidoxyethylammonium iodide (6), which do not penetrate the Blood Brain Barrier, potentiate the effects of threshold doses of analgesics, antidepressant, antishock and antihypoxic agents without any side effects and complications. This is due to stimulation of gastric vagus afferents. Among the drawbacks of the method there should be mentioned the insufficient potentiation of the CNS active drugs when administered at threshold doses. Although potentiation occurs, it does not reach the level of the maximal effect of the CNS drug tested.

Another drawback is the complexity of the synthesis and high cost of the polymers comprised in these compositions.

In rats under urethan anesthesia, peripherally administered serotonin. produced cardiopulmonary reflex. Administration of phenylephrine or adrenaline to anaesthesized rats potentiated 5–10 fold the cardiopulmonary reflex caused by injection of serotonin in short-sleeping rats (7). This is a peripheral rather than a CNS effect, since peripherally administered serotonin cannot penetrate the hematoencephalic barrier.

U.S. Pat. No. 4,631,284 discloses acetaminophen compositions containing a substantially high amount of acetaminophen and a low amount of pheniramine maleate. This patent teaches a method of tabletting using such. compositions.

SUMMARY OF THE INVENTION

It is an object of the invention to provide a pharmaceutical composition comprising a CNS active drug whose activity is potentiated.

It is a further object of the invention to provide a method for potentiating CNS active drugs.

In a first aspect of the invention, there is provided a pharmaceutical composition for systemic administration comprising: (a) an effective dose of a drug which affects the central nervous system (CNS); (b) a compound which affects peripheral chemoreceptors; and (c) a stimulator of osmoreceptors.

It has suprisingly been found that the activity of systemically administered CNS drugs may be significantly potentiated by the co-administration of a compound which affects peripheral chemoreceptors and a stimulator of osmoreceptors. The "active ingredients" of the invention are the CNS drug and the potentiating element, i.e. compound which effects peripheral chemoreceptors and a stimulator of osmoreceptors.

In the present specification, a CNS active drug is a drug that modifies the function of the CNS by directly affecting the CNS or a portion thereof Such drugs include but are not limited to analgesics, antidepressants, neuroleptics, tranquilizers, psychostimulants, hypnotic drugs, anti-parkinson and anti-convulsive agents.

Examples of types of compounds which affect peripheral chemoreceptors are $\alpha$-1-adrenomimetics and catecholamines. Non-limiting examples of $\alpha$-1-adrenomimetics are the compounds phenylephrine and midodrine Non-limiting examples of catecholamines are epinephrine, norepinephrine, dopamine, serotonin amid their combination.

Non limiting examples of stimulators of osmoreceptors include PVP, dextran PEO, xylitol, mannitol, sorbitol, or a combination of two or more stimulators.

The term "effective dose" with respect to the CNS drug refers to an amount of the drug which is effective in bringing about a desired effect in the CNS. This amount may be within the usual dosage range of the drug, or it may be less than the usual dosage range of the drug, due to the potentiating effect(s) of the additional components of the composition.

The composition of the invention is systemically administered to the subject (patient). Techniques of administration include systemic parenteral (e.g. intravenous, intramuscular, subcutaneous, inhalation) and systemic enteral (e.g. oral, sublingual, rectal) administration.

In a second aspect of the invention, there is provided a pharmaceutical composition for systemic administration comprising: (a) an effective dose of a drug which affects the central nervous system (CNS); and (b) a compound which affects peripheral chemoreceptors; wherein the dose of the drug in the composition is less than tile usual dose of the drug.

In this aspect of the invention, the "effective dose" of the drug is less the usual, conventional dosage range of the drug. The usual dose of a CNS drug may be ascertained by reference to standard drug and pharmacological handbooks, such as *Goodman & Gilman's The Pharmacological Basis of Therapeutics* 9th ed. Hardman Paperback, McGraw-Hill Book Company, 1996, the Physician's Desk Reference, the Israel Drug Index, or drug product inserts provided by the drug manufacturer. This information is well known and available to the average skilled man of the art.

In the present invention, the term "composition" may be understood in its usual meaning, i.e. a product of mixing or combining the active ingredients, or the term may be understood as meaning that the active ingredients are administered separately but within a period of time which allows them to interact in the body. For example, in the second aspect of the invention, the compound which affects peripheral chemoreceptors and the CNS active drug may be administered either both parenterally or both orally or else one of them parenterally and the other orally. In the first aspect of the invention, the CNS active drug, the compound which affects peripheral chemoreceptors and the stimulator of osmoreceptors may be administered either all enterally or all parenterally, or else one of them parenterally and the other two enterally, or the reverse.

Preferred compositions according to the invention comprise $\alpha$-1-adrenomimetic and PVP or dextran for intramuscular administration, and α-1-adrenomimetic and xylitol, PVP or dextran for oral administration.

In a third aspect of the invention, there is provided a method of potentiating the activity of a drug which affects the CNS comprising systemically administrating to a subject the drug together with an effective amount of a compound which affects peripheral chemoreceptors and, optionally, with an effective amount of a stimulator of osmoreceptors.

An "effective amount" of a compound which affects peripheral chemoreceptors or a stimulator of osmoreceptors as used in the method of the invention is an amount which results in a significant decrease of a minimal effective dose of the CNS drug administered together with these components. For example, the effective amount of a peripherical chemoreceptor stimulating component administered together with a CNS active drug may decrease by 10–100 fold the minimal effective dose of a CNS active drug required in order to elicit a maximal therapeutic effect (i.e. potentiates the effect of the CNS active drug threshold dose to give the effect of a maximal dose). The effective amount may also be an amount that potentiates the magnitude of the maximal effect of the CNS drug. Including the osmoreceptor stimulator into the composition results in a substantial additional decrease in the effective dose of the CNS active drug.

Preferred concentration ranges (in weight %) of the active ingredients in a composition according to the invention for systemic parenteral administration are as follows: for the CNS active drug: from 0.0005% to the upper limit of the usual dose for each drug: for α-1-adrenomimetic: from 0.0005% to 0.04%, and for stimulants of osmoreceptors from 0.1% to 10%. Compositions for oral administration preferably comprise each active ingredient in the amount of 0.0001% to 10% of the total weight of the composition. The remaining weight of the composition may comprise standard excipients.

In a fourth aspect of the invention, there is provided a method of treating a disease affecting the CNS comprising systemically administrating to a subject an effective dose of a drug which affects the CNS together with an effective amount of a compound which affects peripheral chemoreceptors and an effective amount of a stimulator of osmoreceptors.

In a fifth aspect of the invention, there is provided a method of treating a disease affecting the CNS comprising systemically administrating to a subject an effective dose of a drug which affects the CNS together with an. effective amount of a compound which affects peripheral chemoreceptors, wherein the dose of the drug in the composition is less than the usual dose of the drug.

In a sixth aspect of the invention, there is provided a method for preparing a pharmaceutical composition for systemic administration of a drug which affects the CNS, said method comprising adding to an effective dose of said drug a compound which affects peripheral chemoreceptors; and a stimulator of osmoreceptors.

DETAILED DESCRIPTION OF PREFERRED EMBODIMENTS

Materials and Methods

The potentiation of the effect of CNS active drugs was studied in experiments on breedless white male rats having a mass of 180–200 g. For these studies, solutions of the composition of the invention were used, which. were prepared using distilled water immediately before administration. The solutions were administered either orally (IG), by a rigid metal probe into the cardiac section of the stomach at a total amount of 0.8 ml, or intramuscularly (IM) at an amount of 0.2 ml, 30 min before testing.

To determine the potentiation effect of the composition on the CNS drug, a minimal effective dose of the CNS drug within the composition causing a maximal possible effect for a given model was determined. The potentiation degree was estimated by the magnitude of the decrease in the minimal effective dose of the CNS drug within the composition causing the given effect of CNS active drug.

The analgesic effect of the components was estimated by an extension of the latent period of the reflex of tail flicking in the "tail-flick" test [Woolf C. J., Barret G. D., Mitchel D., Myers R. A. (1977) Eur. J. Pharmacol. 45(3);311–314] and of the reflex of hind leg flicking in the hyperalgesia test [Coderre T. J., Melzack R. Brain Res. (1987) 404(1–2) :95–106].

For the "tail-flick" test, hyperalgesic rats were selected (latent period of tail flicking on placing into water with a temperature of 51° C. was 3–4 sec). To estimate the potentiation effect of Dipyrone or morphine, the minimal effective dose of these drugs in compositions causing a maximal analgesia was determined (latent period of the reflex above 30 s).

Hyperalgesia of a leg was developed by placing it into hot water (56° C.) for 20–25 sec under the conditions of ether anesthesia. Hyperalgesia was developed 30 min. after the burn (latent period of leg flick reflex on its being placed into water at a temperature 47° C. was reduced from 15–20 s to 2–4 s). To estimate the potentiation effect of Dipyrone, the minimal effective dose of Dipyrone in the composition causing a maximal analgesic effect was determined (latent period of the leg-flick reflex above 30s).

Antidepressive effects was studied by Porsolt's test [Porsolt R. D., Anton G., Blavet N., Jalfre M. Eur. J. Pharmacol.(1978), 47(4):379–91]. For each rat under study, the total immobilization time was determined during 10 min of forced swimming in a glass vessel at a water temperature of 22° C. The animals were subdivided into three groups according to their immobilization time: highly-, medium- and low-active (immobilization time below 80 sec. 100–140 sec and above 150 sec, respectively). For a repeated study by Porsolt's test, on the second day low-active and highly active rats were selected.

A model of depression was created by administration to a group of highly active rats of the neurotoxin 1-methyl-4-phenyl-1,2,3,6-tetrahydropyridine (MPTP) [Krupina N. A., Orlova. I. N., Kryzhanovskii G. N. Biull. Eksp. Biol. Med. (1995) 120(8): 160–3] 30 min before testing at a dose of 15 mg/kg. In the 30 min after the administration of MPTP, MPTP depression was developed in 100% of the highly active rats, since they passed into the category of low-active "depressive" rats (immobilization time—above 150 sec). Antidepressants (amitriptyline or Fluoxetine), as well as their compositions were administered to highly active rats 30 minutes before MPTP administration. (60 min before a repeated examination in Porsolt's test), and also to low-active rats 30 min. before a repeated study in Porsolt's test.

To determine the degree of potentiation of the effect of antidepressants, their minimal effective dose within the compositions, which caused a maximal antidepressive effect (immobilization time—below 80 s) in low-active rats and in rats with MPTP-depression was determined.

In a forced swimming test, the ability of amitriptyline and its compositions to eliminate the effect of toxic doses of MPTP was studied. Single administration of high MPTP doses (30 mg/kg) causes acute suppression of motor activity (akinesis), catalepsy, and muscular rigidity. Antidepressants reduce behavioral depression caused by a single administration of toxic doses of MPTP. The behavioral depression was studied in a forced swimming test of a group of active rats after the administration of a toxic dose of MPTP (30 mg/kg IM). Swimming duration (maximal swimming duration—10 min) and the time of forced immobilization during the first 5 min of swimming (under the condition that swimming duration exceeds 5 min) was estimated in the forced swimming test 30 min after MPTP administration. Drugs were administered IM or IG 30 min before MPTP administration.

To estimate the potentiation of the effects of amitriptyline (its ability to reduce toxic effects of MPTP), the minimal effective dose of amitriptyline in the composition, which increased swimming time up to 9–10 min and reduced immobilization time during the first 5 min of swimming down to 20–30 sec was determined.

Haloperidol catalepsy is a test for selecting anti-parkinson agents [Campbell A., Baldessarini R. J. Cremens M. C. *Neuropharmacology* (1988), 27(11):1197–9; Ossowska K. *J. Neural. Transm. Park. Dis. Dement. Sect.* (1994) 8(1–2):39–71]. Catalepsy degree was estimated by the immobilization time (in sec) of a rat placed on a coarse-mesh grid at an angle of 45° during a 3-minute exposition [Campbell A., Baldessarini R. J., Cremens M. C. *Neuropharmacology* (1988) 27(11):1197–9 ] 30, 60, 90 and 120 minutes after haloperidol administration. Maximal catalepsy was attained in 40–60 minutes after haloperidol administration (immobilization time on the grid was 140–180 sec) and lasted from 2 to 6 hours depending on the dose of haloperidol (1 or 3 mg/kg). The minimal effective dose of the anti-parkinson agent memantine causing a maximal anticataleptic effect (immobilization time on an inclined grid less than 40 sec) 1 hour after haloperidol administration at a dose of 1 and 3 mg/kg was calculated.

To estimate the potentiation effect of memantine, the minimal effective dose of memantine in the composition causing a maximal anticataleptic effect was determined.

Anticonvulsive effects of drugs and their compositions was studied on the model of pentetrazole seizures [Parsons C. G . Quack G., Bresink I., Baran L., Przegalinski F., Kostowski. W., Krzascik P., Hartmann. S., Danysz W. *Neuropharmacology* (1995) 34(10):1239–1258). The capacity of the anticonvulsive drug diazepam and its compositions to prevent generalized clonico-tonic and clonic seizures in 80% of the rats 30 minutes after pentetrazole administration at a dose of 70 mg/kg IM (minimal effective dose) was estimated.

To estimate the potentiation of diazepam effect, its minimal effective dose in the composition preventing clonico-tonic and clonic seizures in 80% of rats was determined.

Antipsychotic effect of neuroleptics was studied using the model of behavioral toxicity "MK-toxicity" caused by a blocker of NMDA receptors MK-801 (Lapin T. P., Rogawski M. A. *Behav. Brain Res.* (1995) 70(2):145–151) and a model of phenaminic stereotypy caused by phenamine (Kuczenski R., Schmidt D, Leith N. *Brain Res.* (1977), 126(1): 117–129).

The minimal effective dose of the neuroleptic haloperidol necessary to completely prevent the development of "MK-toxicity" (MK-801 at a dose of 0.4 mg/kg IM) and phenaminic stereotypy (phenamine at a dose of 10 mg/kg IM) in 80% of the rats was calculated. To estimate the potentiation of the antipsychotic effect of haloperidol, the minimal effective dose of haloperidol in compositions, which completely prevents the development of MK-toxicity and phenaminic stereotypy in rats, was determined.

The potentiation of the effect of psychostimulants was studied using the model of phenaminic stereotypy [Kuczenski R., Schmidt D., Leith N. *Brain Res.* (1977), 126(1):117–29]. Phenamine at a dose of 10 mg/kg IM, or 20 mg/kg IG, causes a marked behavioral stereotypy. To estimate the potentiation effect of phenamine, a phenamine dose in the IM or IG introduced composition was determined, which causes the same stereotypy as phenamine alone at a dose of 10 mg/kg, IM or 20 mg/kg, IG. The potentiation degree of the psychostimulating effect of phenamine was estimated by the magnitude of the decrease of an equally effective dose of phenamine in the composition.

EXAMPLES

Example 1

Potentiation of the effect of Analgesics a. Intramuscular administration of compositions A non-narcotic analgesic named Dipyrone at a dose of 20 mg/kg and the narcotic analgesic morphine at a dose of 3 mg/kg completely eliminate algesia in the tail-flick test (latent period of tail-flicking reflex increases from 3 to 30 sec and more). In the hyperalgesia test Dipyrone does not cause complete analgesia even in a limiting dose of 40 mg/kg (latent period of leg flicking reflex increases from 3–4 s to 12.6 s). The results of administrating compositions in accordance with the invention are summarized in Table I.

The $\alpha$-1-adrenomimetics phenylephrine or midodrine at a threshold dose (0.008–0.01 mg/kg), which does not affect analgesia, in a composition with Dipyrone decrease the minimal effective dose of the drug 100 and 132 fold, respectively, causing maximal analgesia in the tail-flick test. In the hyperalgesia test, they potentiate the incomplete effect of the maximal dose of Dipyrone (30 mg/kg), which leads to the development of maximal analgesia in this model, that is more rigorous than the tail-flick model (the latent period of leg flicking reflex becomes longer than 30 s). An increase in $\alpha$-1-adrenomimetic dose up to 0.02 mg/kg does not considerably increase the effect of Dipyrone in the tail-flick test, but decreases the minimal effective dose of Dipyrone causing a maximal analgesic effect in the hyperalgesia test 6–6.9 fold.

Inclusion of a stimulant of osmoreceptors, such as PVP, dextran or PEO, into the composition of Dipyrone with the $\alpha$-1-adrenomimetics phenylephrine or midodrine at a dose that does not cause analgesia leads to an additional 2–3.5-fold decrease in the minimal effective dose of Dipyrone, as well as a 3.3–4-fold decrease of a dose of phenylephrine or midodrine in the composition.

Concentrations of the active ingredients in a solution of the composition of the invention potentiating the effect of Dipyrone were as follows: Dipyrone—from 0.005% to 3%, $\alpha$-1-adrenomimetics—from 0.003% to 0.02%, and stimulants of osmoreceptors—from 0.25% to 2%. A decrease in the contents of $\alpha$-1-adrenomimetics and stimulants of osmoreceptors in a composition with Dipyrone below the indicated limits leads to a dramatic decrease in the composition activity, whereas an increase in their concentration does not lead to a considerable intensification of the effect of the composition.

The minimal effective dose of morphine in the tail-flick test decreases 75-fold in a composition with threshold doses of phenylephrine, and 214-fold in a composition with threshold doses of phenylephrine and PVP.

b. Intragastric (oral) administration of compositions

In the tail-flick test, Dipyrone at a dose of 20 mg/kg and morphine at a dose of 3 mg/kg cause a maximal analgesia (latent period of tail flicking reflex exceeds 30 s). In the hyperalgesia test, IG administration of Dipyrone at its maximal possible dose of 40 mg/kg causes a mild analgesic effect (latent period of tail-flicking reflex—13 s).

Phenylephrine or midodrine at a threshold dose of 0.004–0.005 mg/kg in a composition with Dipyrone decreases its minimal effective dose, causing maximal analgesia in tail-flick test 133–167 times. In the hyperalgesia test they potentiate a mild analgesic effect of the maximal dose of Dipyrone (29 mg/kg) up to a complete analgesia (the latent period of leg flicking reflex becomes longer than 30 s).

A further increase in phenylephrine or midodrine dose up to 0.01 mg/kg in the hyperalgesia test causes not only a potentiation of the effect of Dipyrone, but also decreases 9 and 7.9 times, respectively, the minimal effective dose of Dipyrone in the composition.

Inclusion of stimulants of osmoreceptors such as PVP, dextran, PEO, xylitol or sorbitol into the composition of Dipyrone with α-1-adrenomimetics at a dose that does not cause analgesia leads to an additional 2.3–4.6-fold decrease in the minimal effective dose of Dipyrone and also to a 2.5–5-fold decrease in the threshold dose of phenylephrine or midodrine in the composition.

Concentrations of the active ingredients in a solution of the composition for potentiation were as follows: Dipyrone—from 0.003% to 3%, α-1-adrenomimetics—from 0.001% to 0.01%, and stimulants of osmoreceptors—from 0.1% to 0.8%. A decrease in the contents of α-1-adrenomimetics and stimulants of osmoreceptors in a composition with. Dipyrone below the indicated limits leads to a drastic decrease in the composition activity, whereas an increase in their concentration does not lead to a considerable potentiation of the effect of the composition.

The minimal effective dose of morphine in the tail-flick test decreases 100-fold in a composition with threshold doses of phenylephrine, and 300-fold—in a composition with threshold doses of phenylephrine and xylitol.

TABLE I

Potentiation of analgesic effect of morphine and Dipyrone

| Dipyrone | IM*** | 0.20 ± 2.2 mg/kg | 40 mg/kg**** |
|---|---|---|---|
| Dipyrone + | IM | 5.5 ± 0.6 mg/kg | 31 ± 3.4 mg/kg |
| phenylephrine | IM | 0.004 mg/kg | 0.008 mg/kg |
| Dipyrone + | IM | 0.20 ± 0.023 mg/kg | 5.2 ± 0.56 mg/kg |
| phenylephrine | IM | 0.01 mg/kg | 0.02 mg/kg |
| Dipyrone + | IM | 5.1 ± 0.55 mg/kg | 29 ± 3.2 mg/kg |
| midodrine | IM | 0.004 mg/kg | 0.008 mg/kg |
| Dipyrone + | IM | 0.15 ± 0.018 mg/kg | 4.2 ± 0.46 mg/kg |
| midodrine | IM | 0.01 mg/kg | 0.02 mg/kg |
| Dipyrone + | IM | 0.06 ± 0.007 mg/kg | 1.6 ± 0.19 mg/kg |
| phenylephrine + | IM | 0.003 mg/kg | 0.005 mg/kg |
| PVP | IM | 5 mg/kg | 10 mg/kg |
| Dipyrone + | IM | 0.05 ± 0.006 mg/kg | 1.2 ± 0.15 mg/kg |
| midodrine + | IM | 0.003 mg/kg | 0.005 mg/kg |
| PVP | IM | 5 mg/kg | 10 mg/kg |
| Dipyrone + | IM | 0.06 ± 0.007 mg/kg | 1.9 ± 0.22 mg/kg |
| phenylephrine + | IM | 0.003 mg/kg | 0.005 mg/kg |
| dextran | IM | 2.5 mg/kg | 5 mg/kg |
| Dipyrone + | IM | 0.09 ± 0.01 mg/kg | 2.5 ± 0.29 mg/kg |
| phenylephrine + | IM | 0.003 mg/kg | 0.005 mg/kg |
| PEO | IM | 10 mg/kg | 20 mg/kg |
| Dipyrone | IG***** | 20 ± 2.3 mg/kg | 40 mg/kg****** |
| Dipyrone + | IG | 7.1 ± 0.74 mg/kg | 34.2 ± 3.6 mg/kg |
| phenylephrine | IG | 0.002 mg/kg | 0.004 mg/kg |
| Dipyrone + | IG | 0.12 ± 0.014 mg/kg | 3.8 ± 0.4 mg/kg |
| phenylephrine | IG | 0.005 mg/kg | 0.01 mg/kg |
| Dipyrone + | IG | 6.5 ± 0.72 mg/kg | 32.2 ± 3.6 mg/kg |
| midodrine | IG | 0.002 mg/kg | 0.004 mg/kg |
| Dipyrone + | IG | 0.15 ± 0.0 18 mg/kg | 4.1 ± 0.45 mg/kg |
| midodrine | IG | 0.005 mg/kg | 0.01 mg/kg |

TABLE I-continued

Potentiation of analgesic effect of morphine and Dipyrone

| Dipyrone + | IG | 0.05 ± 0.0068 mg/kg | 1.2 ± 0.14 mg/kg |
|---|---|---|---|
| phenylephrine + | IG | 0.001 mg/kg | 0.002 mg/kg |
| PVP | IG | 8 mg/kg | 1.6 mg/kg |
| Dipyrone + | IG | 0.04 ± 0.005 mg/kg | 1.4 ± 0.16 mg/kg |
| phenylephrine + | IG | 0.001 mg/kg | 0.002 mg/kg |
| dextran | IG | 4 mg/kg | 8 mg/kg |
| Dipyrone + | IG | 0.05 ± 0.0055 mg/kg | 1.9 ± 0.23 mg/kg |
| phenylephrine + | IG | 0.001 mg/kg | 0.002 mg/kg |
| PEO | IG | 16 mg/kg | 32 mg/kg |
| Dipyrone + | IG | 0.03 ± 0.004 mg/kg | 0.8 ± 0.09 mg/kg |
| phenylephrine + | IG | 0.001 mg/kg | 0.002 mg/kg |
| xylitol | IG | 4 mg/kg | 8 mg/kg |
| Dipyrone + | IG | 0.05 ± 0.006 mg/kg | 1.0 ± 0.12 mg/kg |
| midodrine + | IG | 0.001 mg/kg | 0.002 mg/kg |
| xylitol | IG | 4 mg/kg | 8 mg/kg |
| Dipyrone + | IG | 0.06 ± 0.07 mg/kg | 2.5 ± 0.20 mg/kg |
| phenylephrine + | IG | 0.001 mg/kg | 0.002 mg/kg |
| sorbitol | IG | 8 mg/kg | 16 mg/kg |
| Morphine | IM | 3.0 ± 0.37 mg/kg | |
| Morphine + | IM | 2.4 ± 0.028 mg/kg | |
| phenylephrine | IM | 0.004 mg/kg | |
| Morphine + | IM | 0.04 ± 0.0045 mg/kg | |
| phenylephrine | IM | 0.01 mg/kg | |
| Morphine+ | IM | 0.014 ± 0.0017 mg/kg | |
| phenylephrine + | IM | 0.003 mg/kg | |
| PVP | IM | 5 mg/kg | |
| Morphine | IG | 3 ± 0.35 mg/kg | |
| Morphine + | IG | 0.8 ± 0.09 mg/kg | |
| phenylephrine | IG | 0.002 mg/kg | |
| Morphine + | IG | 0.03 ± 0.0035 mg/kg | |
| phenylephrine | IG | 0.005 mg/kg | |
| Morphine + | IG | 0.01 ± 0.0012 mg/kg | |
| phenylephrine + | IG | 0.001 mg/kg | |
| xylitol | IG | 4 mg/kg | |

*Latent period of tail flicking reflex more than 30 sec.
**Latent period of leg flicking reflex more than 30 sec.
***Hereinafter the IM administered volume is 0.2 ml.
****Latent period of leg flicking reflex 12.6 ± 1.4 sec.
*****Hereinafter the IG administered volume is 0.8 ml.
******Latent period of leg flicking reflex 13.1 ± 1.6 sec.

Example 2

Potentiation of the effect of Antidepressants a. Intramuscular administration of compositions IM administration of the antidepressant amitriptyline causes a maximal antidepressive effect in Porsolt's test (during 10 min of forced swimming, the immobilization time is below 80 s) both in a group of low-active rats and in a group of highly active rats with MPTP depression (MPTP—15 mg/kg IM) at doses of 5.0 and 7.2 mg/kg, respectively. An increase of MPTP dose up to 30 mg/kg causes an acute suppression of motor activity and behavioral depression 15–30 min after IM administration. In a forced swimming test, the duration of swimming decreases from 550–600 s to 157–160 s.

Amitriptyline at a dose of 20 mg/kg does not influence the effects of toxic doses of MPTP. Amitriptyline at a maximal dose of 30 mg/kg only partially decreases the toxic effect of MPTP, increasing swimming duration up to 410 s. The total immobilization time after the administration of 30 mg/kg of amitriptyline with 30 mg/kg of MPTP during the first 5 min of swimming was equal to 61 s. This corresponds to the immobilization time of medium-active rats and testifies to a mild antidepressive effect of amitriptyline in the maximal dose in case of administration of toxic doses of MPTP. The results of administrating compositions in accordance with the invention are summarized in Tables II and III.

Phenylephrine or midodrine at a threshold dose (0.002–0.003 mg/kg) in a composition with amitriptyline decrease the minimal effective dose of amitriptyline causing maximal antidepressive effect in low-active rats and rats with MPTP-depression (MPTP 15 mg/kg IM) 87 and 70 times, respectively. Subsequent to the administration of a toxic dose of MPTP (30 mg/kg IM), phenylephrine at a threshold dose of 0.003 mg/kg in the composition with amitriptyline (30 mg/kg) potentiates a mild effect of amitriptyline in the maximal dose and eliminates completely the behavioral depression caused by the toxic dose of MPTP (swimming time increases up to 565 s, and the immobilization time is reduced from 61 s to 28 s). An increase of a dose of phenylephrine up to 0.006 mg/kg in the composition with amitriptyline makes it possible to decrease 3-fold the maximal effective dose of amitriptyline, which totally eliminates the effect of the toxic dose of MPTP.

Additional inclusion of a stimulant of osmoreceptors into the composition of amitriptyline with α-1-adrenomimetic allows decreasing both the minimal effective dose of amitriptyline (2.5–3.3-fold) and the dose of α-1-adrenomimetic (2–3.3-fold), which is observed in all the models under study.

Active ingredient contents in solution of the compositions for potentiation was as follows: amitriptyline—from 0.002% to 3%, α-1-adrenomimetics—from 0.0006% to 0.006%, and stimulants of osmoreceptors—from 0.5% to 2%. A decrease in the contents of α-1-adrenomimetics and stimulants of osmoreceptors in a composition with amitriptyline below the indicated limits leads to a drastic decrease in the composition activity, whereas an increase in their concentration does not lead to a considerable potentiation of the effect of the composition.

IM administration of Fluoxetine causes a maximal antidepressive effect in low-active rats and rats with MPTP depression at a doses of 10.6 and 16.2 mg/kg, respectively. The minimal effective dose of Fluoxetine in Porsolt's test in a composition with phenylephrine and PVP is decreased 46–63-fold.

b. Intragastric administration of compositions

IG administration of amitriptyline causes a maximal antidepressive effect in Porsolt's test (immobilization time below 80 s during 10 min of forced swimming) both in a group of low-active rats and in a group of highly active rats with MPTP depression (IM 15 mg/kg of MPTP) at a dose of 2–2.5 mg/kg respectively. Amitriptyline at a dose of 30 mg/kg IG in the forced swimming test only partially eliminates the behavioral depression caused by a toxic dose of MPTP (30 mg/kg IM) (swimming time increased from 157 s to 340 s in comparison with reference group, and the immobilization time during 5 min of swimming amounted to 78 s).

Phenylephrine or midodrine at a threshold dose of 0.002–0.003 mg/kg) in a composition with amitriptyline decrease 25–33-fold the minimal effective dose of amitriptyline causing a maximal antidepressive effect in low-active rats and rats with MPTP-depression. On the administration of a toxic dose of MPTP (30 mg/kg IM), phenylephrine at a threshold dose of 0.004 mg/kg in the composition with amitriptyline (30 mg/kg) potentiates the incomplete effect of amitriptyline at the maximal dose and eliminates completely the behavioral depression caused by a toxic dose of MPTP (swimming time increases up to 560 s, and the immobilization time is reduced from 78 s to 30 s) An increase in phenylephrine dose up to 0.008 mg/kg in composition with amitriptyline makes it possible to decrease 3-fold the minimal effective dose of amitriptyline, eliminating completely the effect of the toxic dose of MPTP.

Addition of a stimulant of osmoreceptors to the composition of amitriptyline with α-1-adrenomimetic makes it possible to decrease both the minimal effective dose of amitriptyline (2.2–4-fold) and the dose of α-1-adrenomimetic (2–5-fold) in all the models under study.

Active ingredient contents in solutions of the compositions for potentiation was as follows: amitriptyline—from 0.001% to 3%, α-1-adrenomimetics—from 0.0005% to 0.008%, and stimulants of osmoreceptors—from 0.2% to 1%. A decrease in the contents of α-1-adrenomimetics and stimulants of osmoreceptors in a composition with amitriptyline below the indicated limits leads to a drastic decrease in the composition activity, whereas an increase in their concentration does not lead to a considerable potentiation of the effect of the composition.

IG administration of Fluoxetine causes a maximal antidepressive effect in low-active rats and rats with MPTP depression at doses of 5.5 mg/kg and 10.7 mg/kg respectively. The minimal effective dose of Fluoxetine in Porsolt's test in a composition with phenylephrine and PVP decreases 50–59-fold.

TABLE II

Potentiation of antidepressive effect of amitriptyline and Fluoxetine in Porsolt's test

| | | | |
|---|---|---|---|
| Amitriptyline | IM***** | 5.2 ± 0.6 mg/kg | 7.0 ± 0.8 mg/kg |
| Amitriptyline + | IM | 2.1 ± 0.24 mg/kg | 2.4 ± 0.27 mg/kg |
| phenylephrine | IM | 0.001 mg/kg | 0.0015 mg/kg |
| Amitriptyline + | IM | 0.06 ± 0.0066 mg/kg | 0.1 ± 0.013 mg/kg |
| phenylephrine | IM | 0.002 mg/kg | 0.003 mg/kg |
| Amitriptyline + | IM | 3.1 ± 0.34 mg/kg | 4.2 ± 0.47 mg/kg |
| midodrine | IM | 0.001 mg/kg | 0.0015 mg/kg |
| Amitriptyline + | IM | 0.1 ± 0.012 mg/kg | 0.12 ± 0.014 mg/kg |
| midodrine | IM | 0.002 mg/kg | 0.003 mg/kg |
| Amitriptyline + | IM | 0.02 ± 0.0023 mg/kg | 0.03 ± 0.0035 mg/kg |
| phenylephrine + | IM | 0.0006 mg/kg | 0.001 mg/kg |
| PVP | IM | 10 mg/kg | 10 mg/kg |
| Amitriptyline + | IM | 0.03 ± 0. mg/kg | 0.04 ± 0.005 mg/kg |
| midodrine + | IM | 0.0006 mg/kg | 0.001 mg/kg |
| PVP | IM | 10 mg/kg | 10 mg/kg |
| Amitriptyline + | IM | 0.02 ± 0.003 mg/kg | 0.03 ± 0.0035 mg/kg |
| phenylephrine + | IM | 0.001 mg/kg | 0.0015 mg/kg |
| dextran | IM | 5 mg/kg | 5 mg/kg |
| Amitriptyline + | IM | 0.025 ± 0.004 mg/kg | 0.04 ± 0.005 mg/kg |
| phenylephrine + | IM | 0.001 mg/kg | 0.0015 mg/kg |

TABLE II-continued

Potentiation of antidepressive effect of amitriptyline and Fluoxetine in Porsolt's test

| | | | |
|---|---|---|---|
| PEO | IM | 15 mg/kg | 15 mg/kg |
| Fluoxetine | IM | 10.6 ± 1.2 mg/kg | 16 ± 2.1 mg/kg |
| Fluoxetine + PVP | IM IM | 1.4 ± 0.17 mg/kg 20 mg/kg | 1.9 ± 0.23 mg/kg 20 mg/kg |
| Fluoxetine + phenylephrine + PVP | IM IM IM | 0.12 ± 0.015 mg/kg 0.001 mg/kg 10 mg/kg | 0.17 ± 0.021 mg/kg 0.001 mg/kg 10 mg/kg |
| Amitriptyline | IG****** | 2.0 ± 0.24 mg/kg | 2.5 ± 0.5 mg/kg |
| Amitriptyline + phenylephrine | IG IG | 0.92 ± 0.095 mg/kg 0.001 mg/kg | 1.1 ± 0.25 mg/kg 0.0015 mg/kg |
| Amitriptyline + phenylephrine | IG IG | 0.06 ± 0.0065 mg/kg 0.002 mg/kg | 0.10 ± 0.012 mg/kg 0.003 mg/kg |
| Amitriptyline + midodrine | IG IG | 1.2 ± 0.15 mg/kg 0.001 mg/kg | 1.3 ± 0.15 mg/kg 0.0015 mg/kg |
| Amitriptyline + midodrine | IG IG | 0.06 ± 0.0067 mg/kg 0.002 mg/kg | 0.11 ± 0.013 mg/kg 0.003 mg/kg |
| Amitriptyline + phenylephrine + xylitol | IG IG IG | 0.016 ± 0.0021 mg/kg 0.0005 mg/kg 8 mg/kg | 0.03 ± 0.0035 mg/kg 0.001 mg/kg 8 mg/kg |
| Amitriptyline + midodrine + xylitol | IG IG IG | 0.018 ± 0.0022 mg/kg 0.0005 mg/kg 8 mg/kg | 0.035 ± 0.0041 mg/kg 0.001 mg/kg 8 mg/kg |
| Amitriptyline + phenylephrine + PVP | IG IG IG | 0.022 ± 0.0026 mg/kg 0.0007 mg/kg 12 mg/kg | 0.04 ± 0.0045 mg/kg 0.001 mg/kg 12 mg/kg |
| Amitriptyline + phenylephrine + dextran | IG IG IG | 0.012 ± 0.0014 mg/kg 0.0005 mg/kg 8 mg/kg | 0.018 ± 0.0023 mg/kg 0.001 mg/kg 8 mg/kg |
| Amitriptyline + phenylephrine + PEO | IG IG IG | 0.025 ± 0.003 mg/kg 0.0007 mg/kg 32 mg/kg | 0.045 ± 0.0053 mg/kg 0.0014 mg/kg 32 mg/kg |
| Amitriptyline + phenylephrine + sorbitol | IG IG IG | 0.025 ± 0.0029 mg/kg 0.0006 mg/kg 16 mg/kg | 0.038 ± 0.0046 mg/kg 0.0012 mg/kg 16 mg/kg |
| Fluoxetine | IG | 5.5 ± 0.7 mg/kg | 10.7 ± 1.1 mg/kg |
| Fluoxetine + xylitol | IG IG | 1.8 ± 0.23 mg/kg 20 mg/kg | 32 ± 0.36 mg/kg 20 mg/kg |
| Fluoxetine + phenylephrine + xylitol | IG IG IG | 0.11 ± 0.013 mg/kg 0.001 mg/kg 8 mg/kg | 0.18 ± 0.022 mg/kg 0.001 mg/kg 8 mg/kg |

*Minimal effective dose of drug causing a maximal antidepressive effect (immobilization time below 80 sec).
**Total immobilization time more than 140 sec during 10 min of forced swimming in Porsolt's test.
***Total immobilization time below 80 sec during 10 min of forced swimming in Porsolt's test.
****MPTP in the dose of 15 mg/kg IM 30 min after its administration prolongs the immobilization time up to 150 and more seconds during 10 min of forced swimming in Porsolt's test.
*****Hereinafter the IM administered volume is 0.2 ml.
******Hereinafter the IG administered volume is 0.8 ml.

TABLE III

Potentiation of amitriptyline effect in a forced swimming test in rats with behavioral depression caused by a toxic dose of MPTP

| | | | | |
|---|---|---|---|---|
| Distilled water | IM*** | — | 160 ± 22 | — |
| Amitriptyline | IM | 20 | 220 ± 25 | — |
| Amitriptyline | IM | 30 | 410 ± 46 | 61 ± 6.3 |
| Amitriptyline + phenylephrine | IM IM | 30 0.002 | 560 ± 63 | 28 ± 3.0 |
| Amitriptyline + phenylephrine | IM IM | 10 0.006 | 565 ± 61 | 25 ± 2.7 |
| Amitriptyline + phenylephrine + PVP | IM IM IM | 5 0.003 20 | 590 ± 65 | 17 ± 1.9 |
| Distilled water | IG**** | — | 157 ± 18 | — |
| Amitriptyline | IG | 30 | 340 ± 37 | 78 ± 8.5 |
| Amitriptyline + phenylephrine | IG IG | 30 0.004 | 565 ± 59 | 30 ± 3.4 |
| Amitriptyline + phenylephrine | IG IG | 10 0.008 | 558 ± 64 | 28 ± 3.2 |
| Amitriptyline + phenylephrine + xylitol | IG IG IG | 5 0.004 40 | 585 ± 61 | 20 ± 2.3 |

*Duration of forced swimming of rats in sec until drowning 30 min after MPTP administration in the dose of 30 mg/kg to active rats. Maximal recorded time of forced swimming 600 seconds.
**Immobilization time was recorded during the first 5 minutes of forced swimming, 30 min after MPTP administration in the dose of 30 mg/kg to active rats.
***Hereinafter the IM administered volume is 0.2 ml.
****Hereinafter the IG administered volume is 0.8 ml.

Example 3

Potentiation of the effect of Antiparkinson Agents a. Intramuscular administration of compositions The anti-parkinson agent memantine at a dose of 7.5 mg/kg completely eliminates the catalepsy caused by haloperidol at a dose of 1 mg/kg (immobilization time of a rat on an inclined grid is below 40 s). However, even at a dose of 15 mg/kg, memantine eliminates the catalepsy caused by haloperidol at a dose of 3 mg/kg only partially (immobilization time—60–70 s). The results of administrating compositions in accordance with the invention are summarized in Table IV.

Phenylephrine or midodrine at a threshold dose (0.02 mg/kg) in a composition with memantine decrease its minimal effective dose causing a maximal effect (total elimination of catalepsy caused by haloperidol at a dose of 1 mg/kg) 18.8 and 17.9 times, respectively. They also potentiate an incomplete effect of memantine in the maximal dose (15 mg/kg) up to a complete elimination of catalepsy caused by haloperidol at a dose of 3 mg/kg. Further increase of a dose of phenylephrine or midodrine up to 0.04 mg/kg, which also does not cause an independent effect not only potentiates the effect of memantine, but also decreases its maximal effective dose 4.5–4.8 times eliminating catalepsy caused by haloperidol at a dose of 3 mg/kg.

The inclusion of stimulants of osmoreceptors—PVP, dextran or PEO—into the composition with memantine and α-1-adrenomimetics causes an additional decrease in the minimal effective dose of memantine for both models of catalepsy 2.1–2.7 times and at a dose of α-1-adrenomimetic in a tertiary composition 3–4 times.

Active ingredient contents in solutions of the compositions for potentiation was as follows: memantine—from 0.015% to 1.5%, α-1-adrenomimetics—from 0.005% to 0.04%, and stimulants of osmoreceptors—from 1% to 4%. A decrease in the contents of α-1-adrenomimetics and stimulants of osmoreceptors in a composition with memantine below the indicated limits leads to a drastic decrease in the composition activity, whereas an increase in the concentration does not lead to a considerable Potentiation of the effect of the composition.

b. Intragastric administration of composition

Memantine at a dose of 11.5 mg/kg eliminates completely the catalepsy caused by haloperidol at a dose of 1 mg/kg (immobilization time of a rat on an inclined grid is below 40 s). However, at a dose of 16 mg/kg, memantine eliminates the catalepsy caused by haloperidol at a dose of 3 mg/kg only partially (immobilization time—60–70 s).

Phenylephrine or midodrine at a threshold dose of 0.02 mg/kg) in a composition with memantine decrease 10–11 -fold its minimal effective dose causing a maximal effect (total elimination of catalepsy caused by haloperidol at a dose of 1 mg/kg). They also potentiate the incomplete effect of memantine in the maximal dose (16 mg/kg) up to a complete elimination of catalepsy caused by haloperidol at a dose of 3 mg/kg.

A further increase of a threshold dose of phenylephrine or midodrine up to 0.04 mg/kg causes both the potentiation of the effect of memantine and a 3.7–4-fold decrease of its minimal effective dose eliminating catalepsy caused by haloperidol at a dose of 3 mg/kg.

The inclusion of stimulants of osmoreceptors—PVP, dextran, PEO, xylitol or sorbitol—into the composition with memantine and α-1-adrenomimetic causes an additional decrease of the minimal effective dose of memantine in both models of catalepsy 2.1–4 times and the dose of α-1-adrenomimetic 4 times.

Active ingredient contents in solutions of the compositions for potentiation was as follows: memantine—from 0.02% to 1.6%, α-1-adrenomimetics—from 0.005% to 0.04%, and stimulants of osmoreceptors—from 1% to 10%. A decrease in the contents of α-1-adrenomimetics and stimulants of osmoreceptors in a composition with memantine below the indicated limits leads to a drastic decrease in the composition activity, whereas an increase in their concentration does not lead to a considerable potentiation of the effect of the composition.

TABLE IV

Potentiation of the effect of antiparkinson drugs

| | | | |
|---|---|---|---|
| Memantine | IM*** | 7.5 ± 0.7 mg/kg | 15.0 mg/kg**** |
| Memantine + phenylephrine | IM IM | 5.7 ± 0.6 mg/kg 0.01 mg/kg | 13.5 ± 1.5 mg/kg 0.02 mg/kg |
| Memantine + phenylephrine | IM IM | 0.4 ± 0.045 mg/kg 0.02 mg/kg | 3.1 ± 0.04 mg/kg 0.04 mg/kg |
| Memantine + midodrine | IM IM | 6.2 ± 0.7 mg/kg 0.01 mg/kg | 13.8 ± 1.5 mg/kg 0.02 mg/kg |
| Memantine + midodrine | IM IM | 0.42 ± 0.05 mg/kg 0.02 mg/kg | 3.3 ± 0.37 mg/kg 0.04 mg/kg |
| Memantine + phenylephrine + PVP | IM IM IM | 0.15 ± 0.02 mg/kg 0.005 mg/kg 10 mg/kg | 1.3 ± 0.17 mg/kg 0.01 mg/kg 20 mg/kg |
| Memantine + midodrine + PVP | IM IM IM | 0.17 ± 0.021 mg/kg 0.005 mg/kg 10 mg/kg | 1.4 ± 0.17 mg/kg 0.01 mg/kg 10 mg/kg |
| Memantine + phenylephrine + dextran | IM IM IM | 0.18 ± 0.022 mg/kg 0.005 mg/kg 10 mg/kg | 1.4 ± 0.16 mg/kg 0.01 mg/kg 20 mg/kg |
| Memantine + phenylephrine + PEO | IM IM IM | 0.19 ± 0.023 mg/kg 0.005 mg/kg 20 mg/Kg | 1.5 ± 0.18 mg/kg 0.015 mg/kg 40 mg/kg |
| Memantine | IG***** | 11.5 ± 1.2 mg/kg | 16.0 mg/kg**** |
| Memantine + phenylephrine | IG IG | 8.5 ± 0.9 mg/kg 0.01 mg/kg | 15.0 ± 1.7 mg/kg 0.02 mg/kg |
| Memantine + phenylephrine | IG IG | 1.0 ± 0.12 mg/kg 0.02 mg/kg | 4.0 ± 0.046 mg/kg 0.04 mg/kg |
| Memantine + midodrine | IG IG | 8.8 ± 0.9 mg/kg 0.01 mg/kg | 15.2 ± 1.8 mg/kg 0.02 mg/kg |
| Memantine + midodrine | IG IG | 1.1 ± 0.13 mg/kg 0.02 mg/kg | 4.3 ± 0.05 mg/kg 0.04 mg/kg |
| Memantine + phenylephrine + xylitol | IG IG IG | 0.24 ± 0.047 mg/kg 0.005 mg/kg 80 mg/kg | 1.5 ± 0.18 mg/kg 0.01 mg/kg 120 mg/kg |
| Memantine + midodrine + xylitol | IG IG IG | 0.26 ± 0.03 mg/kg 0.005 mg/kg 80 mg/kg | 1.6 ± 0.19 mg/kg 0.01 mg/kg 120 mg/kg |
| Memantine + phenylephrine + PVP | IG IG IG | 0.28 ± 0.034 mg/kg 0.005 mg/kg 40 mg/kg | 1.8 ± 0.22 mg/kg 0.01 mg/kg 80 mg/kg |
| Memantine + phenylephrine + dextran | IG IG IG | 0.2 ± 0.024 mg/kg 0.005 mg/kg 40 mg/kg | 1.3 ± 0.15 mg/kg 0.01 mg/kg 80 mg/kg |
| Memantine + phenylephrine + PEO | IG IG IG | 0.35 ± 0.044 mg/kg 0.005 mg/kg 200 mg/kg | 2.0 ± 0.24 mg/kg 0.01 mg/kg 400 mg/kg |
| Memantine + phenylephrine + sorbitol | IG IG IG | 0.32 ± 0.036 mg/kg 0.005 mg/kg 160 mg/kg | 1.9 ± 0.23 mg/kg 0.01 mg/kg 320 mg/kg |

*Dose of the drug corresponding to the immobilization time of a rat on an inclined grid (at an angle of 45°) below 40 seconds.
**Haloperidol in the doses of 1 mg/kg and 3 mg/kg IM causes after 60 minutes the immobilization of rats on an inclined grid for 140–180 seconds during 3 minutes of exposition.
***Hereinafter the IM administered volume is 0.2 ml.
****The immobilization time of rats on an inclined grid amounts to 60–70 seconds.
*****Hereinafter the 10 administered volume is 0.8 ml.

Example 4

Potentiation of the effect of Anticonvulsive Agents a. Intramuscular administration of compositions Diazepam at a dose of 6.7 mg/kg completely eliminates the generalized (clonico-tonic) seizures caused by pentylenetetrazole at a dose of 70 mg/kg in 80% of rats. Diazepam at the maximal endurable dose of 10 mg/kg eliminates clonic seizures preceding the generalized seizures caused by pentylenetetrazole at a dose of 70 mg/kg only in 20% of rats. The results of administrating compositions in accordance with the invention are summarized in. Table V.

Phenylephrine or midodrine at a threshold dose (0.012 mg/kg) in a composition with diazepam decrease its minimal effective dose causing a maximal anticonvulsive effect (elimination of clonico-tonic seizures caused by pentylenetetrazole at a dose of 70 mg/kg in 80% of rats) 74 and 85 times, respectively. They also potentiate a mild (only in 20% of rats) anticonvulsive effect of diazepam in the maximal dose (10 mg/kg) with respect to clonic pentylenetetrazole seizures (ensures a complete protection against clonic seizures in 80% of rats).

Further increase of a dose of phenylephrine or midodrine up to 0.024 mg/kg, which also does not cause an independent effect, not only potentiates the effect of diazepam, but also decreases 5.5–6.3 times its minimal effective dose eliminating clonic seizures in 80% of rats.

The inclusion of stimulants of osmoreceptors—PVP, dextran or PEO—into the composition with diazepam and α-1-adrenomimetics causes an additional decrease in the minimal effective dose of diazepam for both kinds of seizures 2.3–4.5 times and at a dose of α-1-adrenomimetic in a tertiary composition 2–2.4 times.

Active ingredient contents in solutions of the compositions for potentiation was as follows: diazepam—from 0.002% to 1%, α-1-adrenomimetics—from 0.005% to 0,024%, and stimulants of osmoreceptors—from 1% to 10%. A decrease in the contents of α-1-adrenomimetics and stimulants of osmoreceptors in a composition with diazepam below the indicated limits leads to a drastic decrease in the composition activity, whereas an increase in their concentration does not lead to a considerable potentiation of the effect of the composition.

b. Intragastric administration of compositions

Diazepam at a dose of 2.5 mg/kg eliminates completely clonico-tonic seizures caused by pentylenetetrazole at a dose of 70 mg/kg in 80% of rats. Diazepam in the maximal dose of 10 mg/kg eliminates clonic seizures preceding the generalized seizures caused by pentylenetetrazole at a dose of 70 mg/kg only in 20% of rats.

Phenylephrine or midodrine at a threshold dose of 0.012 mg/kg) in a composition with diazepam decrease 42 and 50 times, respectively, its minimal effective dose causing a maximal effect with respect to clonico-tonic seizures. They also intensify the anticonvulsive effect of diazepam in the maximal dose (10 mg/kg) with respect to clonic pentylenetetrazole-induced seizures (the number of rats without clonic seizures increasing from 20% to 80%).

A further increase at a threshold dose of phenylephrine or midodrine up to 0.024 mg/kg causes both the potentiation of the effect of diazepam and a 5.0–5.9-fold decrease of its minimal effective dose eliminating clonic seizures in 80% of rats.

The inclusion of stimulants of osmoreceptors—PVP, dextran, PEO, xylitol or sorbitol—into the composition with diazepam and α-1-adrenomimetics causes an additional decrease of the minimal effective dose of diazepam in both kinds of seizures 2.3–4.6 times and a decrease at a dose of α-1-adrenomimetic 2.1–3 times.

Active ingredient contents in solutions of the compositions for potentiation was as follows: diazepam—from 0.0013% to 1%, α-1-adrenomimetics—from 0.004% to 0.024%, and stimulants of osmoreceptors—from 0.5% to 5%. A decrease in the contents of α-1-adrenomimetics and stimulants of osmoreceptors in a composition with diazepam below the indicated limits leads to a drastic decrease in the composition activity, whereas an increase in their concentration does not lead. to a considerable potentiation of the effect of the composition.

TABLE V

Potentiation of anticonvulsive effect of diazepam.

| Diazepam | IM** | 6.7 ± 0.7 mg/kg | 10 mg/kg*** |
|---|---|---|---|
| Diazepam + | IM | 1.2 ± 0.14 mg/kg | 8.8 ± 0.9 mg/kg |
| phenylephrine | IM | 0.006 mg/kg | 0.012 mg/kg |
| Diazepam + | IM | 0.09 ± 0.011 mg/kg | 1.8 ± 0.23 mg/kg |
| phenylephrine | IM | 0.012 mg/kg | 0.024 mg/kg |
| Diazepam + | IM | 0.78 ± 0.084 mg/kg | 8.6 ± 0.95 mg/kg |
| midodrine | IM | 0.006 mg/kg | 0.012 mg/kg |
| Diazepam + | IM | 0.08 ± 0.009 mg/kg | 1.6 ± 0.20 mg/kg |
| midodrine | IM | 0.012 mg/kg | 0.024 mg/kg |
| Diazopam + | IM | 0.03 ± 0.0033 mg/kg | 0.5 ± 0.06 mg/kg |
| phenylephrine + | IM | 0.005 mg/kg | 0.01 mg/kg |
| PVP | IM | 10 mg/kg | 20 mg/kg |
| Diazepam + | IM | 0.02 ± 0.0024 mg/kg | 0.41 ± 0.05 mg/kg |
| midodrine + | IM | 0.005 mg/kg | 0.01 mg/kg |
| PVP | IM | 10 mg/kg | 20 mg/kg |
| Diazepam + | IM | 0.02 ± 0.0026 mg/kg | 0.45 ± 0.055 mg/kg |
| phenylephrine + | IM | 0.005 mg/kg | 0.01 mg/kg |
| dextran | IM | 10 mg/kg | 20 mg/kg |
| Diazepam + | IM | 0.04 ± 0.045 mg/kg | 0.70 ± 0.078 mg/kg |
| phenylephrine + | IM | 0.005 mg/kg | 0.01 mg/kg |
| PEO | IM | 50 mg/kg | 100 mg/kg |
| Diazepam | IG**** | 2.5 ± 0.3 mg/kg | 10 mg/kg*** |
| Diazepam + | IG | 0.82 ± 0.089 mg/kg | 8.6 ± 0.9 mg/kg |
| phenylephrine | IG | 0.006 mg/kg | 0.012 mg/kg |
| Diazepam + | IG | 0.06 ± 0.007 mg/kg | 2.0 ± 0.22 mg/kg |
| phenylephrine | IG | 0.012 mg/kg | 0.024 mg/kg |
| Diazepam + | IG | 0.55 ± 0.062 mg/kg | 8.5 ± 0.88 mg/kg |
| midodrine | IG | 0.006 mg/kg | 0.012 mg/kg |
| Diazepam + | IG | 0.05 ± 0.006 mg/kg | 1.7 ± 0.21 mg/kg |
| midodrine | IG | 0.012 mg/kg | 0.024 mg/kg |
| Diazepam + | IG | 0.02 ± 0.0024 mg/kg | 0.65 ± 0.07 mg/kg |
| phenylephrine + | IG | 0.004 mg/kg | 0.01 mg/kg |
| xylitol | IG | 80 mg/kg | 120 mg/kg |
| Diazopam + | IG | 0.015 ± 0.0017 mg/kg | 0.62 ± 0.07 mg/kg |
| midodrine + | IG | 0.004 mg/kg | 0.01 mg/kg |
| xylitol | IG | 80 mg/kg | 120 mg/kg |
| Diazepam + | IG | 0.022 ± 0.0025 mg/kg | 0.72 ± 0.082 mg/kg |
| phenylephrine + | IG | 0.004 mg/kg | 0.01 mg/kg |
| PVP | IG | 40 mg/kg | 80 mg/kg |
| Diazepam + | IG | 0.013 ± 0.0016 mg/kg | 0.6 ± 0.07 mg/kg |
| phenylephrine + | IG | 0.004 mg/kg | 0.01 mg/kg |
| dextran | IG | 20 mg/kg | 40 mg/kg |
| Diazepam + | IG | 0.026 ± 0.003 mg/kg | 0.82 ± 0.1 mg/kg |
| phenylephrine + | IG | 0.004 mg/kg | 0.01 mg/kg |
| PEO | IG | 120 mg/kg | 200 mg/kg |
| Diazepam + | IG | 0.024 ± 0.028 mg/kg | 0.80 ± 0.094 mg/kg |
| phenylephrine + | IG | 0.004 mg/kg | 0.01. mg/kg |
| sorbitol | IG | 120 mg/kg | 200 mg/kg |

*Minimal dose of diazepam preventing pentylenetetrazol seizures in 80% of rats.
**Hereinafter IM administered volume of the solution is 0.2 ml.
***Prevents clonic pentylenetetrazole seizures in 20% of rats.
****Hereinafter IG administered volume of the solution is 0.8 ml.

Example 5

Potentiation of the effect of Neuroleptics a. Intramuscular administration of compositions The neuroleptic haloperidol at a dose of 0.15 mg/kg completely prevents the development of phenaminic stereotypy in 80% of rats. At a dose of 1 mg/kg haloperidol only partially eliminates behavioral toxicity caused by MK-801 (completely eliminates ataxia in 80% of rats, but insignificantly reduces stereotypy and hyperactivity). The results of administrating compositions in accordance with the invention are summarized in Table VI.

Phenylephrine at a threshold dose (0.02 mg/kg) in a composition with haloperidol decrease its minimal effective dose causing a maximal antipsychotic effect (elimination of phenamine stereotypy in 80% of rats) 10 times, respectively. They also potentiate an incomplete antipsychotic effect of haloperidol in the maximal dose (1 mg/kg) in MK-toxicity test (completely eliminates not only ataxia but also hyperactivity and stereotypy in 80% of rats).

A further increase at a dose of phenylephrine up to 0.04 mg/kg, which also does not cause an independent effect, not only potentiates the effect of haloperidol, but also decreases 4.4 times its minimal effective dose, eliminating MK-toxicity.

The inclusion of a stimulant of osmoreceptors PVP into the composition with haloperidol and phenylephrine causes an additional decrease in the minimal effective dose of haloperidol in both tests of 3.0–3.1 times and at a dose of α-1-adrenomimetic in a tertiary composition) by 4 times.

Active ingredient contents in solutions of the compositions for potentiation was as follows: haloperidol—from 0.0005% to 0.1%, alpha-1-adrenomimetic—from 0.005% to 0.04%, and stimulants of osmoreceptors—from 1% to 2%. A decrease in the contents of phenylephrine and PVP in a composition with haloperidol below the indicated limits leads to a drastic decrease in the composition activity, whereas an increase in their concentration does not lead to a considerable potentiation of the effect of the composition.

b) Intragastric administration of compositions

Neuroleptic haloperidol at a dose of 0.18 mg/kg completely prevents the development of phenaminic stereotypy in 80% of rats, At a dose of 1 mg/kg haloperidol eliminates behavioral toxicity caused by MK-801 only partially (completely eliminates ataxia only).

Phenylephrine at a threshold dose of 0.02 mg/kg in a composition with haloperidol decrease 13 times its minimal effective dose causing a maximal antipsychotic effect (elimination of phenaminic stereotypy in 80% of rats). They also potentiate a partial antipsychotic effect of haloperidol in the maximal dose (1mg/kg) in MK-toxicity test (completely eliminates not only ataxia but also hyperactivity and stereotypy in 80% of rats).

A further increase at a threshold dose of phenylephrine up to 0.04 mg/kg causes both the potentiation of the effect of haloperidol and a 3.8-fold decrease of its minimal effective dose eliminating MK-toxicity.

The inclusion of a stimulant of osmoreceptors PVP into the composition with haloperidol and phenylephrine causes an additional decrease of the minimal effective dose of haloperidol in both tests 3.2–3.3 times and a decrease at a dose of phenylephrine 4 times.

Active ingredient contents in solutions of the compositions for potentiation was as follows: haloperidol—from 0.0005% to 0.1%, α-1-adrenomimetics—from 0.005% to 0.04%, and stimulants of osmoreceptors—from 1% to 2%. A decrease in the contents of phenylephrine and PVP in a composition with haloperidol below the indicated limits leads to a drastic decrease in the composition activity, whereas an increase in their concentration does not lead to a considerable potentiation of the effect of the composition.

TABLE 6

Potentiation of antipsychotic effect of haloperidol

| | | | |
|---|---|---|---|
| Haloperidol | IM*** | 0.15 ± 0.017 mg/kg | 1 mg/kg**** |
| Haloperidol + phenylephrine | IM IM | 0.09 ± 0.01 mg/kg 0.01 mg/kg | 0.89 ± 0.093 mg/kg 0.02 mg/kg |
| Haloperidol + phenylephrine | IM IM | 0.015 ± 0.0017 mg/kg 0.02 mg/kg | 0.22 ± 0.026 mg/kg 0.04 mg/kg |
| Haloperidol + phenylephrine + PVP | IM IM IM | 0.005 ± 0.0006 mg/kg 0.005 mg/kg 10 mg/kg | 0.07 ± 0.0076 mg/kg 0.01 mg/kg 20 mg/kg |
| Haloperidol | IG***** | 0.18 ± 0.022 mg/kg | 1 mg/kg**** |
| Haloperidol + phenylephrine | IG IG | 0.14 ± 0.016 mg/kg 0.01 mg/kg | 0.88 ± 0.095 mg/kg 0.02 mg/kg |
| Haloperidol + phenylephrine | IG IG | 0.016 ± 0.002 mg/kg 0.02 mg/kg | 0.26 ± 0.029 mg/kg 0.04 mg/kg |
| Haloperidol + phenylephrine + PVP | IG IG IG | 0.005 ± 0.00056 mg/kg 0.005 mg/kg 40 mg/kg | 0.08 ± 0.01 mg/kg 0.01 mg/kg 80 mg/kg |

*Phenamine in the dose of 10 mg/kg IM causes a behavioral stereotypy after 30–60 minutes.
**MK-801 (disocylpin) in the dose of 0.4 mg/kg IM causes a strong hyperactivity. stereotypy and ataxia after 20–30 minutes.
***Hereinafter IM administered volume of the solution is 0.2 ml.
****In the dose of 1 mg/kg (IM and IG) haloperidol eliminates ataxia in 80% of rats.
*****Hereinafter IG administered volume of the solution is 0.8 ml.

Example 6

Potentiation of the effect of Psychostimulants

The psychostimulant phenamine at a dose of 10 mg/kg IM and 20 mg/kg IG causes a marked behavioral stereotypy. IM or IG administration of phenamine in the composition with a threshold dose (0.02 mg/kg) of phenylephrine makes it possible to decrease the minimal effective dose of phenamine causing a maximally expressed stereotypy 4–5.3 times. The results of administrating compositions in accordance with the invention are summarized in Table VII.

Additional inclusion of a stimulant of osmoreceptors PVP (IM, IG) into the composition of phenamine with phenylephrine at a doses, which do not potentiate independently the effect of phenamine decreases 2.3–2.4 times the minimal effective dose of phenamine and, at the same time, decrease 3.3–4 times the dose of phenylephrine in the composition.

A decrease at a dose of phenylephrine below 0.002 mg/kg and PVP below 20 mg/kg drastically decreases the activity of compositions with phenamine. An increase at a dose of phenylephrine above 0.02 mg/kg and PVP above 80 mg/kg does not considerably increase the activity of compositions with phenamine but increases the risk of complications.

TABLE VII

Potentiation of phenamine stereotypy in rats

| | | |
|---|---|---|
| Phenamine + distilled water | IM | 10.0 ± 1.1 mg/kg |
| Phenamine + PVP 20 mg/kg | IM | 8.5 ± 0.9 mg/kg |
| Phenamine + phenylephrine 0.01 mg/kg | IM | 9.2 ± 0.97 mg/kg |
| Phenamine + phenylephrine 0.02 mg/kg | IM | 2.5 ± 0.29 mg/kg |
| Phenamine + phenylephrine 0.005 mg/kg + PVP 10 mg/kg | IM | 1.1 ± 0.13 mg/kg |
| Phenamine + distilled water | IG | 20.2 ± 2.3 mg/kg |
| Phenamine + PVP 80 mg/kg | IG | 17.8 ± 1.9 mg/kg |
| Phenamine + phenylephrine 0.01 mg/kg | IG | 16.9 ± 1.8 mg/kg |
| Phenamine + phenylephrine 0.02 mg/kg | IG | 3.8 ± 0.44 mg/kg |
| Phenamine + phenylephrine 0.005 mg/kg + PVP 40 mg/kg | IG | 1.6 ± 0.14 mg/kg |

*Behavioral stereotypy caused by phenamine in the dose of 10 mg/kg IM.
**Hereinafter IM administered volume of the solution is 0.2 ml.
***Hereinafter IG administered volume of the solution is 0.8 ml.

Example 7

Potentiation of CNS drug by Cathecholamines

It may be concluded from Table VII, below, that catecholamines (e.g. epinephrine, dopamine, serotonin) potentiate the anticonvulsive action of (diazepam, threshold doses, when administered i.m. in a double composition with diazepam or triple composition with diazepam and PVP.

TABLE VIII

Potentiation of anticonvulsive effect of diazepam by cathecholamines

| | | |
|---|---|---|
| Diazepam | IM** | 67 ± 0.7 mg/kg |
| Diazepame + epinephrine | IM IM | 1.5 ± 0.18 mg/kg 0.01 mg/kg |
| Diazepame + epinephrine | IM IM | 0.09 ± 0.01 mg\kg 0.02 mg/kg |
| Diazepame + epinephrine + PVP | IM IM IM | 0.09 ± 0.01 mg/kg 0.1 mg/kg 10 mg/kg |
| Diazepame + dopamine | IM IM | 1.3 ± 0.15 mg/kg 0.01 mg/kg |
| Diazepame + dopamine | IM IM | 0.12 ± 0.014 mg/kg 0.02 mg\kg |
| Diazepame + dopamine + PVP | IM IM IM | 0.04 ± 0.0046 mg/kg 0.01 mg\kg 10 mg/kg |
| Diazepame + serotonin | IM IM | 1.4 ± 0.16 mg\kg 0.006 mg\kg |
| Diazepame + serotonin | IM IM | 0.17 ± 0.02 mg\kg 0.012 mg\kg |
| Diazepame + serotonin + PVP | IM IM IM | 0.06 ± 0.007 mg/kg 0.005 mg\kg 10 mg\kg |

*Minimal dose of diazepam preventing pentylenetetrazol seizures in 80% of rats.
**Hereinafter IM administered volume of the solution is 0.2 ml Example 8

Comparison of prior Art Compositions and Composition of the Invention

Although it is known to potentiate CNS active drugs by osmoreceptor simulators, the results obtained by combining the above two components together with a compound which affects peripheral chemoreceptors are significantly and unexpectedly improved, as illustrated in following tables.

TABLE IX

Comparative results of potentiation of analgesic effect of Dipyrone:

| | | | | |
|---|---|---|---|---|
| a | Dipyrone | IM | 1.5 ± 1.8 mg/kg | 20.2 ± 2.3 mg/kg |
| | PVP | IM | 20 mg/kg | 40 mg/kg |
| b | Dipyrone | IM | 0.06 ± 0.007 mg/kg | 1.6 ± 0.19 mg/kg |
| | PVP | IM | 5 mg/kg | 10 mg/kg |
| | phenylephrine | IM | 0.003 mg/kg | 0.005 mg/kg |
| a | Dipyrone | IM | 2.0 ± 0.24 mg/kg | 24.5 ± 2.8 mg/kg |
| | dextran | IM | 10 mg/kg | 20 mg/kg |
| b | Dipyrone | IM | 0.06 ± 0.007 mg/kg | 1.9 ± 0.22 mg/kg |
| | Dextran | IM | 2.5 mg/kg | 5 mg/kg |
| | phenylephrine | IM | 0.003 mg/kg | 0.005 mg/kg |
| a | Dipyrone | IM | 2.5 ± 0.29 mg/kg | 31.2 ± 3.5 mg/kg |
| | PEO | IM | 30 mg/kg | 60 mg/kg |
| b | Dipyrone | IM | 0.09 ± 0.01 mg/kg | 2.5 ± 0.29 mg/kg |
| | PEO | IM | 10 mg/kg | 20 mg/kg |
| | phenylephrine | IM | 0.003 mg/kg | 0.005 mg/kg |
| a | Dipyrone | IG | 6.2 ± 0.7 mg/kg | 20.4 ± 2.2 mg/kg |
| | PVP | IG | 20 mg/kg | 40 mg/kg |
| b | Dipyrone | IG | 0.05 ± 0.0068 mg/kg | 1.2 ± 0.14 mg/kg |
| | PVP | IG | 8 mg/kg | 16 mg/kg |
| | Phenylephrine | IG | 0.001 mg/kg | 0.002 mg/kg |
| a | Dipyrone | IG | 3.9 ± 0.44 mg/kg | 17.5 ± 1.9 mg/kg |
| | Dextran | IG | 10 mg/kg | 20 mg/kg |
| b | Dipyrone | IG | 0.04 ± 0.005 mg/kg | 1.4 ± 0.16 mg/kg |
| | Dextran | IG | 4 mg/kg | 8 mg/kg |
| | phenylephrine | IG | 0.001 mg/kg | 0.002 mg/kg |
| a | Dipyrone | IG | 6.5 ± 0.75 mg/kg | 27.4 ± 2.9 mg/kg |
| | PEO | IG | 40 mg/kg | 80 mg/kg |
| b | Dipyrone | IG | 0.05 ± 0.0055 mg/kg | 1.9 ± 0.23 mg/kg |
| | PEO | IG | 16 mg/kg | 32 mg/kg |
| | phenylephrine | IG | 0.001 mg/kg | 0.002 mg/kg |
| a | Dipyrone | IG | 4.5 ± 0.5 mg/kg | 14.6 ± 1.6 mg/kg |
| | xylitol | IG | 20 mg/kg | 40 mg/kg |
| b | Dipyrone | IG | 0.03 ± 0.004 mg/kg | 0.8 ± 0.09 mg/kg |
| | xylitol | IG | 4 mg/kg | 8 mg/kg |
| | phenylephrine | IG | 0.001 mg/kg | 0.002 mg/kg |
| a | Dipyrone | IG | 5.2 ± 0.58 mg/kg | 18.5 ± 1.9 mg/kg |
| | sorbitol | IG | 40 mg/kg | 80 mg/kg |
| b | Dipyrone | IG | 0.06 ± 0.007 mg/kg | 2.5 ± 0.20 mg/kg |
| | sorbitol | IG | 8 mg/kg | 16 mg/kg |
| | phenylephrine | IG | 0.001 mg/kg | 0.002 mg/kg | a) Dipyrone + osmoreceptor stimulant
b) Dipyrone + osmoreceptor stimulant + peripheral α-1-adrenomimetic ingredient

TABLE X

Comparative results of potentiation of anti-depressive effect of amitryptiline

| | | | | |
|---|---|---|---|---|
| a | Amitriptyline | IM | 0.4 ± 0.45 mg/kg | 0.6 ± 0.07 mg/kg |
|   | PVP | IM | 20 mg/kg | 20 mg/kg |
| b | Amitriptyline | IM | 0.02 ± 0.0023 mg/kg | 0.03 ± 0.0035 mg/kg |
|   | PVP | IM | 10 mg/kg | 10 mg/kg |
|   | phenylephrine | IM | 0.0006 mg/kg | 0.001 mg/kg |
| a | Amitriptyline | IM | 0.3 ± 0.035 mg/kg | 0.5 ± 0.06 mg/kg |
|   | Dextran | IM | 10 mg/kg | 10 mg/kg |
| b | Amitriptyline | IM | 0.02 ± 0.0023 mg/kg | 0.03 ± 0.0035 mg/kg |
|   | Dextran | IM | 5 mg/kg | 5 mg/kg |
|   | phenylephrine | IM | 0.001 mg/kg | 0.0015 mg/kg |
| a | Amitriptyline | IM | 0.5 ± 0.07 mg/kg | 0.8 ± 0.09 mg/kg |
|   | PEO | IM | 30 mg/kg | 30 mg/kg |
| b | Amitriptyline | IM | 0.025 ± 0.003 mg/kg | 0.04 ± 0.005 mg/kg |
|   | PEO | IM | 15 mg/kg | 15 mg/kg |
|   | phenylephrine | IM | 0.001 mg/kg | 0.0015 mg/kg |
| a | Amitriptyline | IG | 0.5 ± 0.06 mg/kg | 0.72 ± 0.084 mg/kg |
|   | PVP | IG | 30 mg/kg | 30 mg/kg |
| b | Amitriptyline | IG | 0.022 ± 0.0026 mg/kg | 0.04 ± 0.0045 mg/kg |
|   | PVP | IG | 12 mg/kg | 1.2 mg/kg |
|   | Phenylephrine + B57 | IG | 0.0007 mg/kg | 0.001 mg/kg |
| a | Amitriptyline | IG | 0.33 ± 0.037 mg/kg | 0.52 ± 0.06 mg/kg |
|   | Dextran | IG | 20 mg/kg | 20 mg/kg |
| b | Amitriptyline | IG | 0.012 ± 0.0014 mg/kg | 0.018 ± 0.0023 mg/kg |
|   | Dextran | IG | 8 mg/kg | 8 mg/kg |
|   | phenylephrine | IG | 0.0005 mg/kg | 0.001 mg/kg |
| a | Amitriptyline | IG | 0.55 ± 0.06 mg/kg | 0.75 ± 0.09 mg/kg |
|   | PEO | IG | 80 mg/kg | 80 mg/kg |
| b | Amitriptyline | IG | 0.025 ± 0.003 mg/kg | 0.045 ± 0.0053 mg/kg |
|   | PEO | IG | 32 mg/kg | 32 mg/kg |
|   | phenylephrine | IG | 0.0007 mg/kg | 0.00014 mg/kg |
| a | Amitriptyline | IG | 0.31 ± 0.035 mg/kg | 0.45 ± 0.05 mg/kg |
|   | xylitol | IG | 20 mg/kg | 20 mg/kg |
| b | Amitriptyline | IG | 0.016 ± 0.0021 mg/kg | 0.03 ± 0.0035 mg/kg |
|   | xylitol | IG | 8 mg/kg | 8 mg/kg |
|   | phenylephrine | IG | 0.0005 mg/kg | 0.001 mg/kg |
| a | Amitriptyline | IG | 0.63 ± 0.071 mg/kg | 0.91 ± 0.1 mg/kg |
|   | sorbitol | IG | 40 mg/kg | 40 mg/kg |
| b | Amitriptyline | IG | 0.025 ± 0.0029 mg/kg | 0.038 ± 0.0046 mg/kg |
|   | sorbitol | IG | 16 mg/kg | 16 mg/kg |
|   | phenylephrine | IG | 0.0006 mg/kg | 0.0012 mg/kg | a) Amitriptyline + osmoreceptor stimulant
b) Amitriptyline + osmoreceptor stimulant + peripheral α-1 adrenomimetic stimulant

TABLE XI

Comparative results of potentiation of antiparkinson effect on memantine:

| | | | |
|---|---|---|---|
| a | Memantine | IM | 1.4 ± 0.16 mg/kg |
|   | PVP | IM | 20 mg/kg |
| b | Memantine | IM | 0.15 ± 0.02 mg/kg |
|   | PVP | IM | 10 mg/kg |
|   | phenylephrine | IM | 0.005 mg/kg |
| a | Memantine | IM | 1.8 ± 0.2 mg/kg |
|   | dextran | IM | 20 mg/kg |
| b | Memantine | IM | 0.18 ± 0.022 mg/kg |
|   | Dextran | IM | 10 mg/kg |
|   | phenylephrine | IM | 0.005 mg/kg |
| a | Memantine | IM | 2.2 ± 0.24 mg/kg |
|   | PEO | IM | 40 mg/kg |
| b | Memantine | IM | 0.19 ± 0.023 mg/kg |
|   | PEO | IM | 20 mg/kg |
|   | phenylephrine | IM | 0.005 mg/kg |
| a | Memantine | IG | 4.5 ± 0.5 mg/kg |
|   | PVP | IG | 80 mg/kg |
| b | Memantine | IG | 0.28 ± 0.034 mg/kg |
|   | PVP | IG | 40 mg/kg |
|   | phenylephrine | IG | 0.005 mg/kg |
| a | Memantine | IG | 4.8 ± 0.54 mg/kg |
|   | dextran | IG | 80 mg/kg |
| b | Memantine | IG | 0.2 ± 0.024 mg/kg |
|   | Dextran | IG | 40 mg/kg |
|   | phenylephrine | IG | 0.005 mg/kg |
| a | Memantine | IG | 4.9 ± 0.55 mg/kg |
|   | PEO | IG | 400 mg/kg |
| b | Memantine | IG | 0.35 ± 0.044 mg/kg |
|   | PEO | IG | 200 mg/kg |
|   | phenylephrine | IG | 0.005 mg/kg |
| a | Memantine | IG | 5.2 ± 0.56 mg/kg |
|   | xylitol | IG | 160 mg/kg |
| b | Memantine | IG | 0.24 ± 0.047 mg/kg |
|   | xylitol | IG | 80 mg/kg |
|   | phenylephrine | IG | 0.005 mg/kg |
| a | Memantine | IG | 5.7 ± 0.63 mg/kg |
|   | sorbitol | IG | 320 mg/kg |
| b | Memantine | IG | 0.32 ± 0.036 mg/kg |
|   | sorbitol | IG | 160 mg/kg |
|   | phenylephrine | IG | 0.005 mg/kg | a) memantine + osmoreceptor stimulant
b) memantine + osmoreceptor stimulant + peripheral α-1 adrenomimetic stimulant

TABLE XII

Comparative results of potentiation of anticonvulsive effect of diazepam:

| | | | |
|---|---|---|---|
| a | diazepam | IM | 1.5 ± 0.17 mg/kg |
| | PVP | IM | 20 mg/kg |
| b | diazepam | IM | 0.03 ± 0.0033 mg/kg |
| | PVP | IM | 10 mg/kg |
| | phenylephrine | IM | 0.005 mg/kg |
| a | diazepam | IM | 1.0 ± 0.12 mg/kg |
| | dextran | IM | 20 mg/kg |
| b | diazepam | IM | 0.02 ± 0.0026 mg/kg |
| | Dextran | IM | 10 mg/kg |
| | phenylephrine | IM | 0.005 mg/kg |
| a | diazepam | IM | 1.3 ± 0.16 mg/kg |
| | PEO | IM | 40 mg/kg |
| b | diazepam | IM | 0.04 ± 0.0045 mg/kg |
| | PEO | IM | 20 mg/kg |
| | phenylephrine | IM | 0.005 mg/kg |
| a | diazepam | IG | 0.4 ± 0.0045 mg/kg |
| | PVP | IG | 80 mg/kg |
| b | diazepam | IG | 0.022 ± 0.0025 mg/kg |
| | PVP | IG | 40 mg/kg |
| | phenylephrine | IG | 0.004 mg/kg |
| a | diazepam | IG | 0.2 ± 0.023 mg/kg |
| | dextran | IG | 40 mg/kg |
| b | diazepam | IG | 0.013 ± 0.0016 mg/kg |
| | Dextran | IG | 20 mg/kg |
| | phenylephrine | IG | 0.004 mg/kg |
| a | diazepam | IG | 0.53 ± 0.58 mg/kg |
| | PEO | IG | 240 mg/kg |
| b | diazepam | IG | 0.026 ± 0.003 mg/kg |
| | PEO | IG | 120 mg/kg |
| | phenylephrine | IG | 0.004 mg/kg |
| a | diazepam | IG | 0.38 ± 0.044 mg/kg |
| | xylitol | IG | 160 mg/kg |
| b | diazepam | IG | 0.02 ± 0.024 mg/kg |
| | xylitol | IG | 80 mg/kg |
| | phenylephrine | IG | 0.004 mg/kg |
| a | diazepam | IG | 0.52 ± 0.055 mg/kg |
| | sorbitol | IG | 240 mg/kg |
| b | diazepam | IG | 0.024 ± 0.0028 mg/kg |
| | sorbitol | IG | 120 mg/kg |
| | phenylephrine | IG | 0.004 mg/kg | a) diazepam + osmoreceptor stimulant
b) diazepam + osmoreceptor stimulant + peripheral α-1 adrenomimetic stimulant

TABLE XIII

Comparative results of potentiation of antipsychotic effect of haloperidol:

| | | | | |
|---|---|---|---|---|
| a | haloperidol | IM | 0.07 ± 0.008 mg/kg | 0.45 ± 0.05 mg/kg |
| | PVP | IM | 20 mg/kg | 40 mg/kg |
| b | haloperidol | IM | 0.005 ± 0.0006 mg/kg | 0.07 ± 0.008 mg/kg |
| | PVP | IM | 10 mg/kg | 20 mg/kg |
| | phenylephrine | IM | 0.005 mg/kg | 0.01 mg/kg |
| a | haloperidol | IG | 0.05 ± 0.006 mg/kg | 0.48 ± 0.055 mg/kg |
| | PVP | IG | 80 mg/kg | 160 mg/kg |
| b | haloperidol | IG | 0.005 ± 0.00056 mg/kg | 0.08 ± 0.01 mg/kg |
| | PVP | IG | 40 mg/kg | 80 mg/kg |
| | phenylephrine | IG | 0.005 mg/kg | 0.01 mg/kg | a) haloperidol + osmoreceptor stimulant
b) haloperidol + osmoreceptor stimulant + peripheral α-1 adrenomimetic stimulant

TABLE XIV

Comparative results of potentiation of psychostimulant effect of phenamine:

| | | | |
|---|---|---|---|
| a | phenamine | IM | 8.5 ± 0.9 mg/kg |
| | PVP | IM | 20 mg/kg |
| b | phenamine | IM | 1.1 ± 0.13 mg/kg |
| | PVP | IM | 10 mg/kg |
| | phenylephrine | IM | 0.005 mg/kg |
| a | phenamine | IG | 17.8 ± 1.9 mg/kg |
| | PVP | IG | 80 mg/kg |
| b | phenamine | IG | 1.6 ± 0.14 mg/kg |
| | PVP | IG | 40 mg/kg |
| | phenylephrine | IG | 0.005 mg/kg | a) phenamine + osmoreceptor stimulant
b) phenamine + osmoreceptor stimulant + peripheral α-1 adrenomimetic stimulant

What is claimed is:

1. A method of potentiating the activity of a drug which affects the CNS, comprising systemically administrating to a subject said drug together with an effective amount of a compound which affects peripheral chemoreceptors selected from the group consisting of a catecholamine, serotonin and the α-1-adrenomimetics phenylephrine and midodrine and, optionally, with an effective amount of a stimulator of osmoreceptors, wherein said stimulator of osmoreceptors is selected from PVP, dextran, PEO, xylitol, mannitol, and sorbitol.

2. A method according to claim 1, wherein said systemic administration is selected from the group of techniques of administration consisting of parenteral, intravenous, intramuscular, subcutaneal, sublingual, rectal and oral.

3. A method according to claim 2, wherein said drug, compound and optional stimulator are each administered by a different technique of administration.

4. A method according to claim 2, wherein said drug, compound and optional stimulator are administered by the same technique of administration.

5. A method according to claim 1, wherein said drug is selected from the group consisting of analgesics, antidepressants, neuroleptics, tranquilizers, psychostimulants, hypnotic drugs, antiparkinson and anticonvulsive agents.

6. A method according to claim 5, wherein said drug is an antidepressant.

7. A method according to claim 1, wherein said compound which affects peripheral chemoreceptors is the α-1-adrenomimetic phenylephrine.

8. A method according to claim 1, wherein said compound which affects peripheral chemoreceptors is a catecholamine.

9. A method according to claim 8, wherein said catecholamine is selected from the group consisting of epinephrine, norepinephrine, dopamine and a combination thereof.

10. A method according to claim 1, wherein an effective amount of said stimulator of osmoreceptors is administered to said subject.

11. A method according to claim 1, wherein said compound which affects peripheral chemoreceptors is the α-1-adrenomimetic midodrine.

12. A method according to claim 1, wherein said compound which affects peripheral chemoreceptors is serotonin.

* * * * *